(12) United States Patent
Okuda et al.

(10) Patent No.: US 8,318,096 B2
(45) Date of Patent: Nov. 27, 2012

(54) BIOLOGICAL SAMPLE MEASUREMENT APPARATUS

(75) Inventors: Eiji Okuda, Ehime (JP); Tooru Aoki, Ehime (JP); Norio Imai, Ehime (JP); Akiyoshi Oozawa, Ehime (JP)

(73) Assignee: Panasonic Corporation, Osaka (JP)

( * ) Notice: Subject to any disclaimer, the term of this patent is extended or adjusted under 35 U.S.C. 154(b) by 228 days.

(21) Appl. No.: 12/528,521

(22) PCT Filed: Dec. 8, 2008

(86) PCT No.: PCT/JP2008/003654
§ 371 (c)(1),
(2), (4) Date: Aug. 25, 2009

(87) PCT Pub. No.: WO2009/075092
PCT Pub. Date: Jun. 18, 2009

(65) Prior Publication Data
US 2010/0035334 A1    Feb. 11, 2010

(30) Foreign Application Priority Data

Dec. 12, 2007 (JP) .............................. 2007-320378
Jan. 9, 2008 (JP) .............................. 2008-001927
Jan. 25, 2008 (JP) .............................. 2008-015643

(51) Int. Cl.
*G01N 15/06* (2006.01)
*G01N 33/00* (2006.01)
*G01N 33/48* (2006.01)

(52) U.S. Cl. ... 422/68.1; 422/50; 422/82.01; 422/82.02; 436/43; 436/63; 436/66

(58) Field of Classification Search ............ 422/50, 422/68.1, 82.01, 82.02; 436/43, 63, 66
See application file for complete search history.

(56) References Cited

U.S. PATENT DOCUMENTS 5,366,609 A * 11/1994 White et al. ............. 204/403.04
6,171,264 B1 * 1/2001 Bader ......................... 600/595
(Continued)

FOREIGN PATENT DOCUMENTS

EP    1 453 212    9/2004
(Continued)

OTHER PUBLICATIONS

International Search Report issued Jan. 27, 2009 in International (PCT) Application No. PCT/JP2008/003654, filed Dec. 8, 2008.

(Continued)

*Primary Examiner* — Brian J Sines
(74) *Attorney, Agent, or Firm* — Wenderoth, Lind & Ponack, L.L.P.

(57) ABSTRACT

A wireless blood glucose meter is a battery-powered apparatus to communicating wirelessly with a portable terminal, and includes a blood glucose level detector that measures a blood glucose level, a transmitter that transmits the blood glucose level measured by the blood glucose level detector to the portable terminal, a receiver that receives a response signal sent from the portable terminal in response to the transmission of the blood glucose level by the transmitter to the portable terminal, and a voltage monitor that monitors the output voltage of the battery. A transmission control circuit changes the transmission method used by the transmitter on the basis of the output voltage of the battery as detected by the voltage monitor.

11 Claims, 9 Drawing Sheets

U.S. PATENT DOCUMENTS

| | | |
|---|---|---|
| 6,558,320 B1 * | 5/2003 | Causey et al. ............... 600/300 |
| 6,641,533 B2 * | 11/2003 | Causey et al. ............... 600/300 |
| 7,261,690 B2 * | 8/2007 | Teller et al. ............... 600/300 |
| 7,643,997 B2 | 1/2010 | Kintzig et al. |
| 2003/0125612 A1 | 7/2003 | Fox et al. |
| 2004/0185821 A1 * | 9/2004 | Yuasa ............... 455/343.5 |
| 2005/0027182 A1 | 2/2005 | Siddiqui et al. |
| 2005/0038332 A1 | 2/2005 | Saidara et al. |
| 2005/0096511 A1 | 5/2005 | Fox et al. |
| 2005/0096512 A1 | 5/2005 | Fox et al. |
| 2005/0113653 A1 | 5/2005 | Fox et al. |
| 2006/0277048 A1 | 12/2006 | Kintzig et al. |
| 2007/0102304 A1 | 5/2007 | Tam |
| 2007/0159321 A1 | 7/2007 | Ogata et al. |
| 2007/0232880 A1 | 10/2007 | Siddiqui et al. |
| 2008/0162054 A1 | 7/2008 | Tam |
| 2008/0165010 A1 | 7/2008 | Tam |

FOREIGN PATENT DOCUMENTS

| | | |
|---|---|---|
| EP | 1 728 470 A1 | 12/2006 |
| EP | 1 728 470 B1 | 12/2008 |
| EP | 1 759 201 | 10/2010 |
| EP | 2 256 494 | 12/2010 |
| EP | 2 256 495 | 12/2010 |
| EP | 2 259 057 | 12/2010 |
| JP | 2002-251461 | 9/2002 |
| JP | 2004-266452 | 9/2004 |
| JP | 2006-208018 | 8/2006 |
| JP | 2007-37983 | 2/2007 |
| JP | 2007-132937 | 5/2007 |
| JP | 2007-184754 | 7/2007 |
| JP | 2007-213308 | 8/2007 |
| JP | 2008-501426 | 1/2008 |
| WO | 02/078512 | 10/2002 |
| WO | 2005/065538 | 7/2005 |

OTHER PUBLICATIONS

Supplementary European Search Report issued Jul. 28, 2011 in corresponding European Application No. 08 85 9378.

* cited by examiner

BIOLOGICAL SAMPLE MEASUREMENT APPARATUS

BACKGROUND OF THE INVENTION

I. Technical Field

The present invention relates to a biological sample measurement apparatus, and more particularly a biological sample measurement apparatus having a wireless communication function.

II. Description Of The Related Art

Various techniques for extending continuous operating time in battery-powered electronic devices have been disclosed in the past.

For example, as shown in the electronic device block diagram of FIG. 11, Japanese Laid-Open Patent Application 2004-266452 discloses that when an automatic battery charge detector 101 has detected that the charge of a battery has dropped to or below a specific value, a central processing controller 102 instructs a wireless communication device 103 to move the communication mode from class 2 (high output level) to class 3 (low output level). At this point, the central processing controller 102 instructs a signal processor 104 to halt some functions. This extends the continuous operating time by cutting back on power consumption.

Patent Citation 1: Japanese Laid-Open Patent Application 2004-266452

SUMMARY OF THE INVENTION

When prior art is used for something like a musical device, music can be reproduced until the battery goes dead, even if there is a drop-off in quality. On the other hand, with a biological sample measurement apparatus, such as a blood glucose meter having a wireless communication function for sending a measurement result to another device, at least the blood glucose level has to be measured accurately, and the power required for this must be ensured.

However, when prior art was used, a problem was that proper measurement could not be performed if the required power could not be ensured and the battery charge dropped low.

In view of this, it is an object of the present invention to be able to perform proper measurement even if the battery charge drops low.

The biological sample measurement apparatus according to the first aspect of the present invention is a battery-powered biological sample measurement apparatus that communicates wirelessly with an external device, and includes a biological data measurement component, a transmitter, a receiver, a voltage monitor, and a transmission controller. The biological data measurement component measures biological data. The transmitter transmits to the external device the biological data measured by the biological data measurement component. The receiver receives response signals sent from the external device in response to the transmission of the biological data from the transmitter to the external device. The voltage monitor monitors the output voltage of the battery. The transmission controller changes the transmission method used by the transmitter on the basis of the output voltage of the battery detected by the voltage monitor.

Here, the transmission controller changes the transmission method used by the transmitter on the basis of the output voltage of the battery detected by the voltage monitor.

Consequently, when the battery charge drops low, for example, the transmission controller controls the transmitter so not to execute the transmission of biological data to an external device, retransmission in the event of unsuccessful transmission of biological data, or the like, and this avoids the consumption of battery power.

As a result, the minimum power required for the biological sample measurement apparatus to measure biological data can be ensured, so measurement can be carried out properly even if the battery charge drops low.

The biological sample measurement apparatus according to the second aspect is the biological sample measurement apparatus according to the first aspect, wherein the transmission controller controls the transmitter so that the transmission of biological data is not executed if the output voltage of the battery as detected by the voltage monitor is lower than a first reference voltage.

Here, how the transmitter is controlled by the transmission controller is specified.

Consequently, if the battery charge drops low, the battery power will not be consumed by the transmission of biological data. As a result, it is possible to extend battery life for measuring biological data.

The biological sample measurement apparatus according to the third aspect is the biological sample measurement apparatus according to the first or second aspect, wherein the transmission controller controls the transmitter so that the retransmission of biological data is executed if the output voltage of the battery as detected by the voltage monitor is equal to or greater than a second reference voltage, when the response signal received by the receiver is not an acknowledge signal indicating that the external device has properly received the biological data, or when the receiver does not receive the response signal within a specific length of time.

Here, how the transmitter is controlled by the transmission controller is specified.

Consequently, it is possible to determine the retransmission of biological data by objectively determining when communication with an external device was not successful. Also, since the retransmission of biological data can be determined on the basis of the output voltage of the battery, it is possible to perform retransmission so that the biological data can be properly transmitted when the battery is sufficiently charged.

The biological sample measurement apparatus according to the fourth aspect is the biological sample measurement apparatus according to any of the first to third aspects, wherein the transmission controller controls the transmitter so that biological data is not retransmitted if the output voltage of the battery as detected by the voltage monitor is lower than a second reference voltage and is equal to or greater than the first reference voltage, when the response signal received by the receiver is not an acknowledge signal, or when the receiver does not receive the response signal within the specific length of time.

Here, how the transmitter is controlled by the transmission controller is specified.

Consequently, it is possible to determine the retransmission of biological data by objectively determining when communication with an external device was not successful. Also, since the retransmission of biological data can be determined on the basis of the output voltage of the battery, it is possible to extend battery life for measuring biological data.

The biological sample measurement apparatus according to the fifth aspect is the biological sample measurement apparatus according to any of the first to fourth aspects, and further includes a reception controller that controls the receiver so that a response signal is not received from an external device if the output voltage of the battery as detected by the voltage monitor is lower than a second reference voltage.

Here, how the receiver is controlled by the reception controller is specified.

Consequently, if the battery charge drops low, the consumption of battery power by the reception of a response signal can be avoided, so it is possible to extend battery life for measuring biological data.

The biological sample measurement apparatus according to the sixth aspect is the biological sample measurement apparatus according to any of the first to fifth aspects, and further includes an interface that has a display component to display the biological data measured by the biological data measurement component, an operation setting component that the user uses to make various operation settings, and an alarm sound output component to output an alarm sound.

The biological sample measurement apparatus according to the seventh aspect is the biological sample measurement apparatus according to the sixth aspect, wherein the interface further has a first display controller to control the display component so that the biological data is not displayed until the transmitter has completed the transmission of the biological data.

Consequently, until the transmission of biological data is complete, at least the area around the display component is kept uncovered by the user's hand so that the user can check his or her own biological data. As a result, the effect of radio wave absorption by the user's hand can be reduced, then the transmission power can be kept low and the service life of the battery can be further extended, since.

The biological sample measurement apparatus according to the eighth aspect is the biological sample measurement apparatus according to the sixth or seventh aspect, wherein the interface further has an alarm sound output controller to control the alarm sound output component so that the alarm sound is outputted when the value of the biological data is equal to or greater than a first reference value, or is less than or equal to a second reference value that is lower than the first reference value.

Consequently, when the measured biological data has a value indicating an emergency situation, for example, people around the user are warned by an alarm sound that the user is in an emergency situation.

The biological sample measurement apparatus according to the ninth aspect is the biological sample measurement apparatus according to any of the sixth to eighth aspects, wherein the interface further has a second display controller to control the display component so that an emergency status is displayed when the value of the biological data is equal to or greater than a first reference value, or is less than or equal to a second reference value that is lower than the first reference value.

Consequently, when the measured biological data has a value indicating an emergency situation, for example, people around the user are warned by a display that there is an emergency situation.

The biological sample measurement apparatus according to the tenth aspect is the biological sample measurement apparatus according to the ninth aspect, wherein the emergency status is a telephone number.

Consequently, the user or people around the user can see the displayed telephone number and immediately contact the family or personal physician of the patient.

The biological sample measurement apparatus according to the eleventh aspect is the biological sample measurement apparatus according to the ninth or tenth aspect, wherein the emergency status is a method of treating hyperglycemia or hypoglycemia.

Consequently, the user or people around the user can provide suitable treatment while looking at the displayed treatment method, etc.

The biological sample measurement apparatus according to the twelfth aspect is the biological sample measurement apparatus according to any of the first to eleventh aspects, which is a wireless blood glucose meter constituted so that the biological data measurement component measures a blood glucose levelblood glucose level.

Here, a wireless blood glucose meter that communicates wirelessly with a portable terminal is applied as a biological sample measurement apparatus.

Consequently, it is possible to provide a wireless blood glucose meter that can properly measure a blood glucose level even if the battery charge drops low.

With the biological sample measurement apparatus according to the present invention, measurement can be carried out properly even if the battery charge drops low.

DETAILED DESCRIPTION OF THE INVENTION

A wireless blood glucose meter (biological sample measurement apparatus) 2 according to an embodiment of the present invention will now be described through reference to FIGS. 1 to 8.

Constitution of Wireless Blood Glucose Meter 2

A blood glucose level (biological data) is measured several times a day with the wireless blood glucose meter 2. The user of the wireless blood glucose meter 2 connects an electrochemical, disposable biosensor 1 to the wireless blood glucose meter 2, and puts a spot of blood on the biosensor 1.

The wireless blood glucose meter 2 detects the blood glucose level from the connected biosensor 1, and sends the detected blood glucose level data to a portable terminal (external device) 3. The portable terminal 3 sends a response signal to the wireless blood glucose meter 2 upon receiving this data. This response signal is usually an acknowledge signal indicating that the blood glucose level data has been received from the wireless blood glucose meter 2, but if some kind of data has been received from the wireless blood glucose meter 2, but blood glucose level data cannot be read due to external disturbance, this is a non-acknowledge signal.

The portable terminal 3 is carried around by a hospital physician or nurse and used to store blood glucose levels measured by the patient. The portable terminal 3 has a function of display these blood glucose levels in a graph so that its transition can be checked, and sending stored blood glucose levels to a server installed in the hospital, etc. through a network Internal Operation of Wireless Blood Glucose Meter 2

The internal operation of the wireless blood glucose meter 2 will now be described through reference to FIG. 1, which is a block diagram of a wireless blood glucose meter and peripheral device in an embodiment of the present invention.

Figure 1:
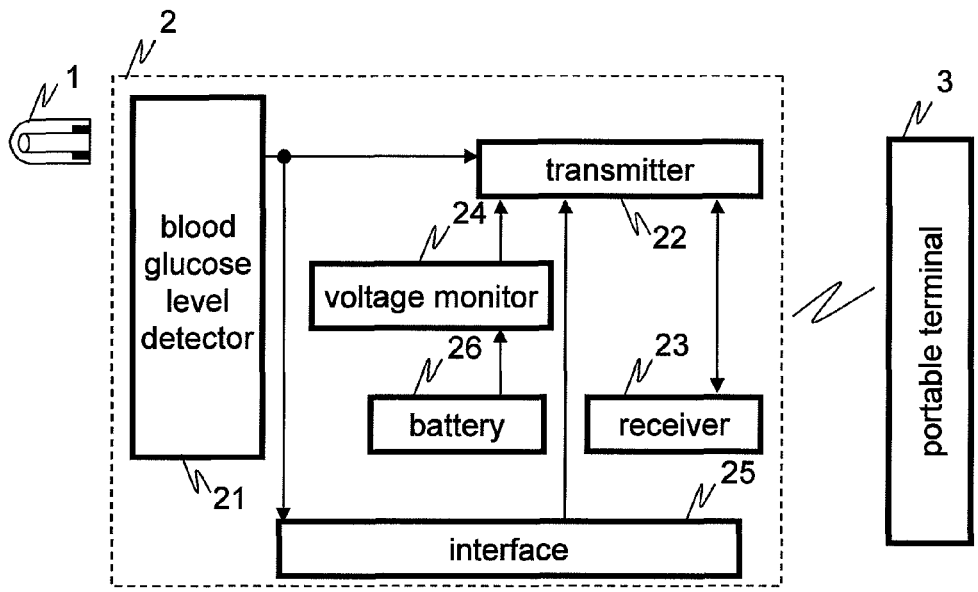
FIG. 1 is a block diagram of a wireless blood glucose meter and peripheral device in an embodiment of the present invention.

As shown in FIG. 1, the wireless blood glucose meter 2 has a blood glucose level detector (biological data measurement component) 21, a transmitter 22, a receiver 23, a voltage monitor 24, an interface 25, and a battery 26.

The blood glucose level detector 21 measures a blood glucose level from a spot of blood placed on the biosensor 1. The blood glucose level thus measured is then transferred to the transmitter 22 and the interface 25.

The transmitter 22 sends the portable terminal 3 the blood glucose level data detected by the blood glucose level detector 21.

Here, the portable terminal 3 sends an acknowledge signal upon receiving blood glucose level data sent from the transmitter 22.

Upon receiving an acknowledge signal from the portable terminal 3, the receiver 23 outputs to the transmitter 22 information indicating that an acknowledge signal has been received. Here, if the receiver 23 cannot receive an acknowledge signal within 600 ms even though the transmitter 22 has sent a blood glucose level to the portable terminal 3, the transmitter 22 sets the transmission power to the highest value possible and resends the blood glucose level data to the portable terminal 3. This retransmission of the blood glucose level data is performed five times at most, until the receiver 23 receives an acknowledge signal. The maximum transmission power at which the transmitter 22 transmits shall be within a range that complies with any applicable legal restrictions.

The voltage monitor 24 monitors the output voltage of the battery 26 installed in the wireless blood glucose meter 2. This allows a transmission control circuit (transmission controller) 221 (discussed below) to perform control according to the output voltage of the battery 26, that is, to the remaining charge of the battery 26. This will be discussed in detail later.

The interface 25 serves as an interface component when the user operates the wireless blood glucose meter 2, and has an operating setting component 251 and a display component 252, for example. The interface 25 will be discussed in detail later.

The battery 26 supplies voltage for driving the various components of the wireless blood glucose meter 2.

Internal Blocks of Wireless Blood Glucose Meter 2

The internal blocks of the wireless blood glucose meter 2 will now be described in detail.

Blood Glucose Level Detector 21

Next, the blood glucose level detector 21 will be described in detail through reference to FIG. 2, which is a block diagram of the blood glucose level detector 21.

Figure 2:
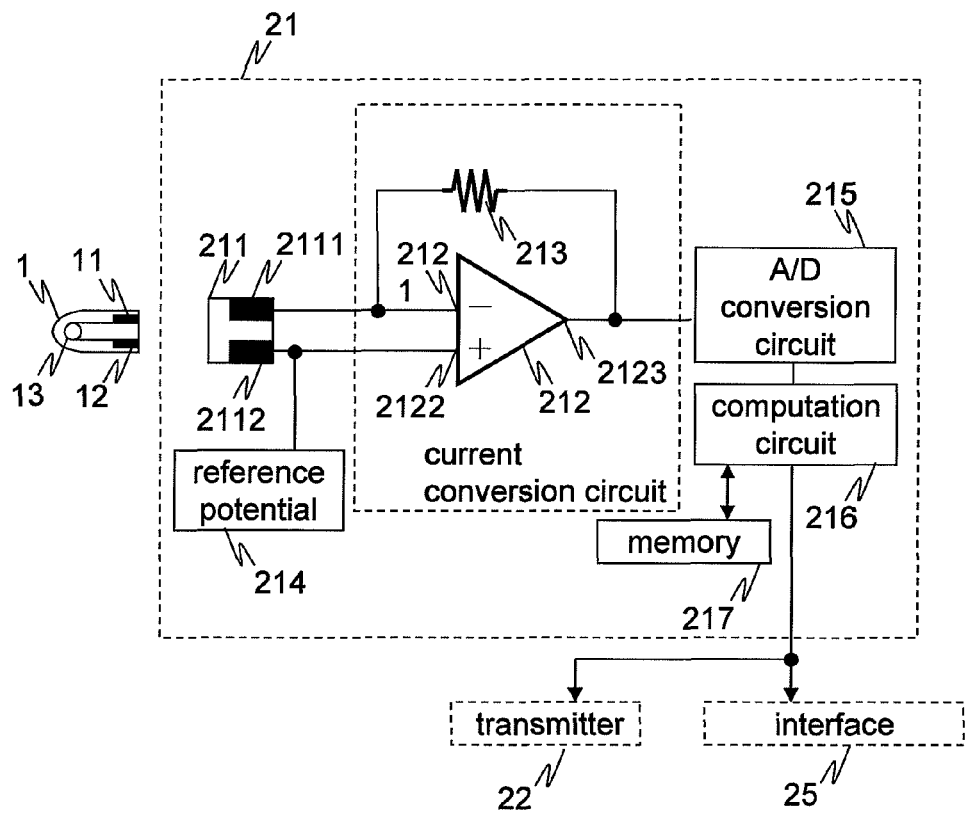
FIG. 2 is a block diagram of a blood glucose level detector in an embodiment of the present invention.

As shown in FIG. 2, the blood glucose level detector 21 has a connector 211, a computation amplifier 212, a feedback resistor 213, an A/D conversion circuit 215, a computation circuit 216, and a memory 217.

The biosensor 1 here is a disposable, electrochemical type, and has a working electrode 11, a counter electrode 12, and a reactant 13. The working electrode 11 comes into contact with an electrode 2111 when the biosensor 1 is inserted into the connector 211. The counter electrode 12 comes into contact with an electrode 2112 when the biosensor 1 is inserted into the connector 211. The reactant 13 is formed from an enzyme, a mediator, or the like. When a spot of blood is placed on the reactant 13, the reactant 13 dissolves in the blood and undergoes an enzyme reaction.

The connector 211 is an insertion opening for inserting the biosensor 1, and has the electrode 2111 and the electrode 2112. When the biosensor 1 is inserted into the connector 211, the electrode 2111 comes into contact with the working electrode 11 included in the biosensor 1, and the electrode 2112 comes into contact with the counter electrode 12 included in the biosensor 1.

The computation amplifier 212 applies voltage to the working electrode 11 and the counter electrode 12 through the electrode 2111 in contact with the working electrode 11 of the biosensor 1 and the electrode 2112 in contact with the counter electrode 12 of the biosensor 1. Current that is correlated to the sugar concentration in the blood flows through the feedback resistor 213 to the biosensor 1 at this point A non-inverting input terminal 2122 of the computation amplifier 212 is connected to a reference potential 214 here. The computation amplifier 212 controls so as to keep the non-inverting input terminal 2122 and an inverting input terminal 2121 at the same potential, so a voltage in which the reference potential 214 is added to the potential drop produced by the current of the feedback resistor 213 is generated at an output terminal 2123. Consequently, a voltage that is proportional to the current flowing to the biosensor 1 is generated, and current-voltage conversion can be performed.

The A/D conversion circuit 215 converts the voltage generated at the output terminal 2123 into a digital value. The A/D conversion circuit 215 sends the converted digital value to the computation circuit 216.

The computation circuit 216 computes the digital value sent from the A/D conversion circuit 215. Consequently, the glucose concentration in the blood can be calculated from the value for the current flowing to the biosensor 1. The computation circuit 216 transfers the calculated glucose concentration to the transmitter 22 and the interface 25.

For example, the following processing is carried out in obtaining the glucose concentration in the blood.

Ahead of time, at the factory, two constant current supplies that generate current equivalent to a low glucose concentration and a high glucose concentration are connected between the electrode 2111 and the electrode 2112 of the connector 211, and a linear conversion expression for the current value and the digital value is found with the computation circuit 216 from the A/D conversion values of each. The slope a and the intercept b of this linear expression are information that correlates the glucose concentration and the digital value outputted from the A/D conversion circuit 215, and this information is stored in the memory 217. Then, when the user measures a blood glucose level, the computation circuit 216 calculates the glucose concentration in the blood by plugging the digital value obtained from the A/D conversion circuit 215 into the linear expression stored in the memory 217. The calculated blood glucose level is transferred to the transmitter 22 and the interface 25.

Transmitter 22

The transmitter 22 will now be described in detail through reference to FIG. 3, which is a block diagram of the transmitter 22, and FIG. 4, which is a control flowchart for the transmitter 22.

Figure 3:
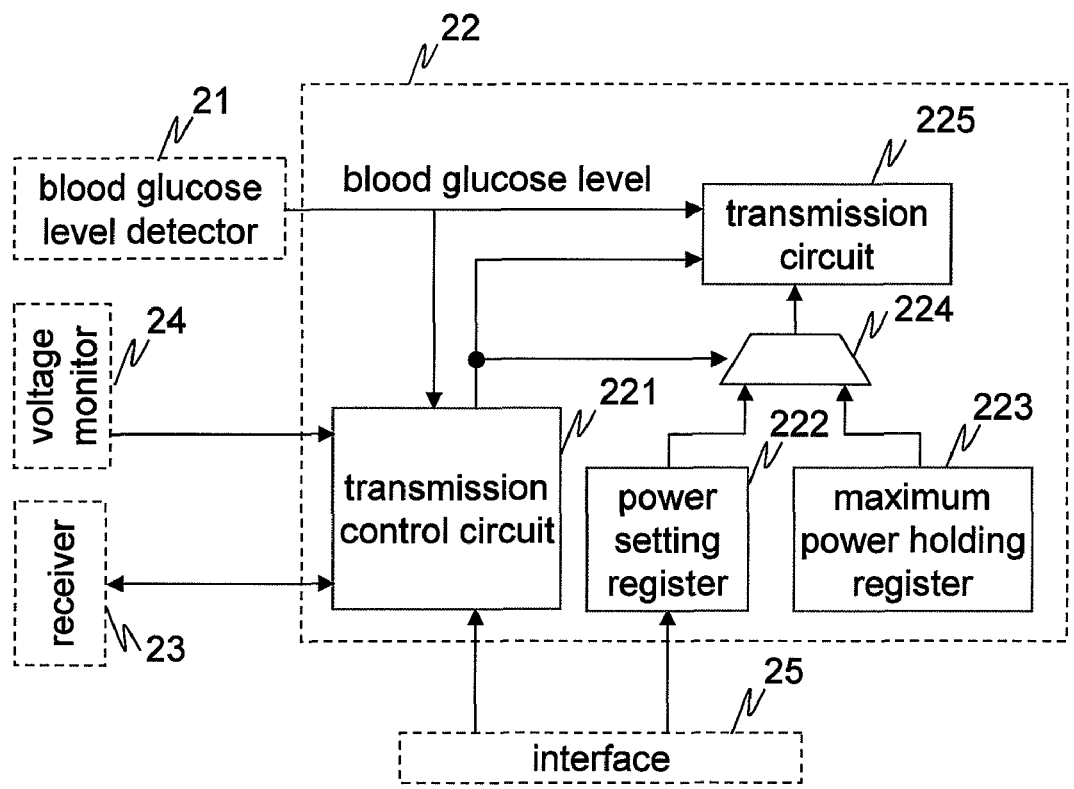
FIG. 3 is a block diagram of a transmitter in an embodiment of the present invention.
Figure 4:
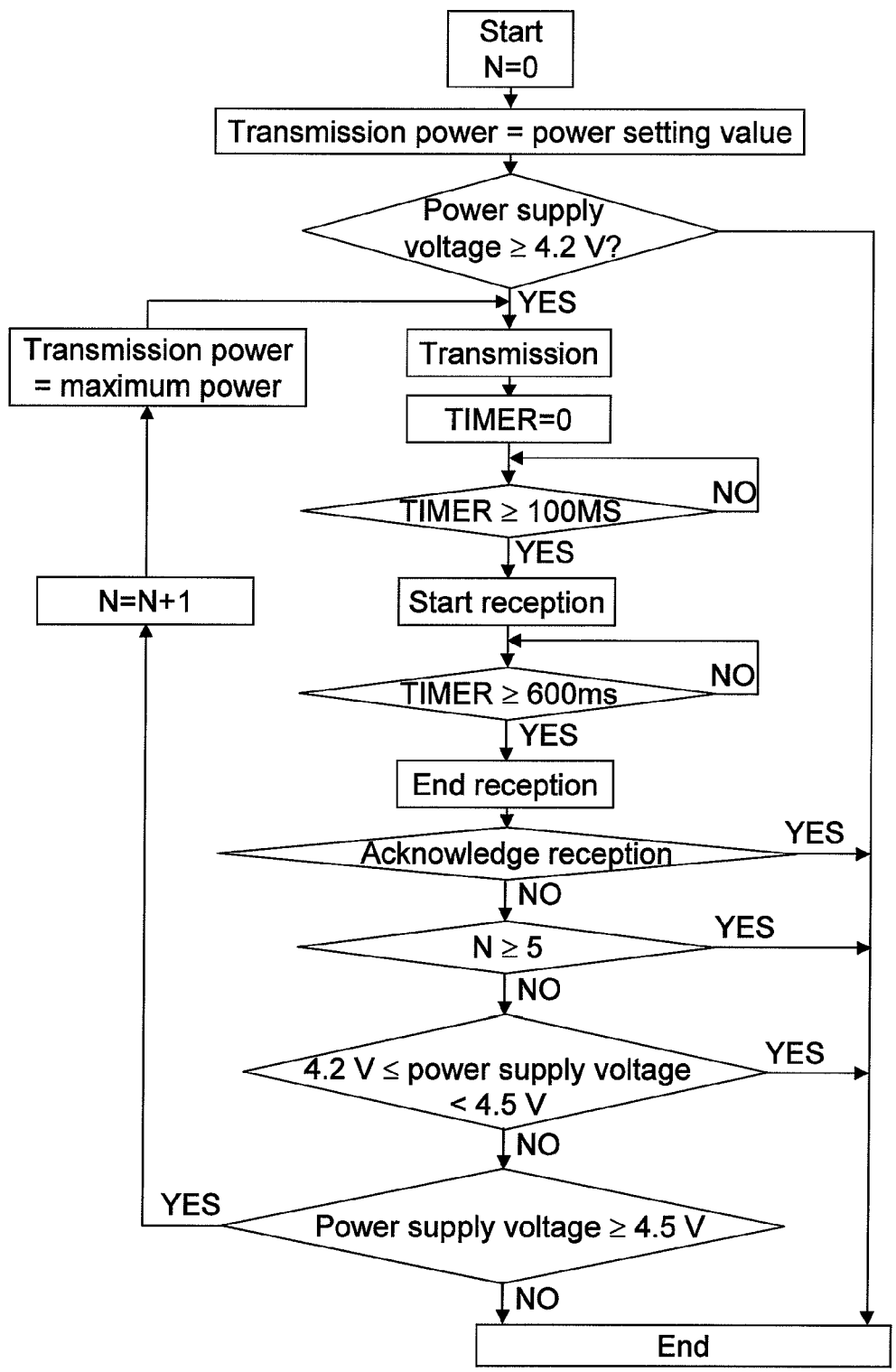
FIG. 4 is a control flowchart of a transmitter in an embodiment of the present invention.

As shown in FIG. 3, the transmitter 22 has a transmission control circuit 221, a power setting register 222, a maximum power holding register 223, a selector 224, and a transmission circuit 225.

The transmission control circuit 221 controls the selector 224 and the transmission circuit 225.

The power setting register 222 holds the transmission power during transmission by a transmission power determination component.

The maximum power holding register 223 holds the maximum transmission power that can be sent by the wireless blood glucose meter 2.

The selector 224 switches the power outputted to the transmission circuit 225 between the power setting register 222 and the maximum power holding register 223.

The transmission circuit 225 takes the blood glucose level data sent from the blood glucose level detector 21 and sends it to the portable terminal 3 at the power sent from the selector 224.

The transmission control circuit 221 changes the transmission method for the transmitter 22 on the basis of the output voltage of the battery 26 monitored by the voltage monitor 24, and instructs the transmission circuit 225 to send the blood glucose level outputted from the blood glucose level detector 21 to the portable terminal 3. More specifically, the transmission control circuit 221 confirms the output voltage of the battery 26 monitored by the voltage monitor 24.

Here, when it has been determined by the voltage monitor 24 that the output voltage of the battery 26 is lower than 4.2 V (the first reference voltage) (BP [1:0] of voltage monitor 24=00), the transmission control circuit 221 does not allow the blood glucose level outputted from the blood glucose level detector 21 to be sent to the portable terminal 3, and ends processing.

When it has been determined by the voltage monitor 24 that the output voltage of the battery 26 is at least 4.2 V (BP [1:0] of voltage monitor 24=01, or BP [1:0] of voltage monitor 24=11), the transmission circuit 225 modulates into transmission data the product of adding an error detection signal to the measurement data, adds a preamble pattern and a sync pattern to the head of this, and sends this to the portable terminal 3. The transmission control circuit 221 issues a command to transmit to the transmission circuit 225, and begins counting with an internal timer. The portable terminal 3 sends out an acknowledge signal 500 ms after the receipt of the blood glucose level data. The transmission control circuit 221 instructs the receiver 23 to begin receiving 100 ms after transmission, and ends the receipt by the receiver 23 600 ms after the start of transmission.

Next, the transmission control circuit 221 check the information whether or not an acknowledge signal has been received with the receiver 23. If the receiver 23 has received an acknowledge signal from the portable terminal 3, the transmission control circuit 221 controls the transmission circuit 225 so that the transmission of the blood glucose level to the portable terminal 3 is ended.

Meanwhile, if the receiver 23 has not received an acknowledge signal from the portable terminal 3, or if it has received a non-acknowledge signal from the portable terminal 3 (that is, if information that an acknowledge signal is not received is outputted from the receiver 23), it is checked the transmission count and whether the output voltage of the battery 26 meets specific conditions (discussed in detail later), and the transmission control circuit 221 switches the selector 224 so that the value stored in the maximum power holding register 223 is inputted to the transmission circuit 225. The transmission control circuit 221 then instructs the transmission circuit 225 to resend the blood glucose level.

The above-mentioned specific conditions will now be explained.

First, the transmission control circuit 221 confirms whether or not the transmission count N of the blood glucose level data is 5 or greater. If the transmission count of the blood glucose level data is 5 or greater, that is, if the blood glucose level has been retransmitted by the transmission circuit 225 five times without being able to receive an acknowledge signal from the portable terminal 3 even once, then the transmission control circuit 221 instructs the transmission circuit 225 to end the transmission of the blood glucose level. That is, the retransmission of the blood glucose level by the transmission circuit 225 is only carried out five times.

On the other hand, if the transmission count of the blood glucose level data is less than 5, the transmission control circuit 221 confirms the output voltage of the battery 26 monitored by the voltage monitor 24.

Here, when it has been determined by the voltage monitor 24 that the output voltage of the battery 26 is at least 4.2 V (the first reference voltage) and lower than 4.5 V (the second reference voltage) (BP [1:0] of voltage monitor 24=01), the transmission control circuit 221 ends the series of processing without instructing that the blood glucose level outputted from the blood glucose level detector 21 be sent to the portable terminal 3. Consequently, power consumption of the battery 26 can be reduced, which makes it possible to further extend the service life of the battery 26.

When it has been determined by the voltage monitor 24 that the output voltage of the battery 26 is at least 4.5 V (BP [1:0] of voltage monitor 24=11), the transmission control circuit 221 switches the selector 224 and sends (resends) the blood glucose level. This allows retransmission to be performed only when the battery 26 still has plenty of charge left.

As indicated above, because the transmission control circuit 221 controls whether or not a blood glucose level is transmitted based on the value of the output voltage monitored by the voltage monitor 24, the battery lasts longer and the blood glucose level measurement function of the wireless blood glucose meter 2 can be maintained.

Receiver 23

Next, the receiver 23 will be described in detail through reference to FIG. 5, which is a block diagram of the receiver 23, and FIG. 6, which is a control flowchart for the receiver 23.

Figure 5:
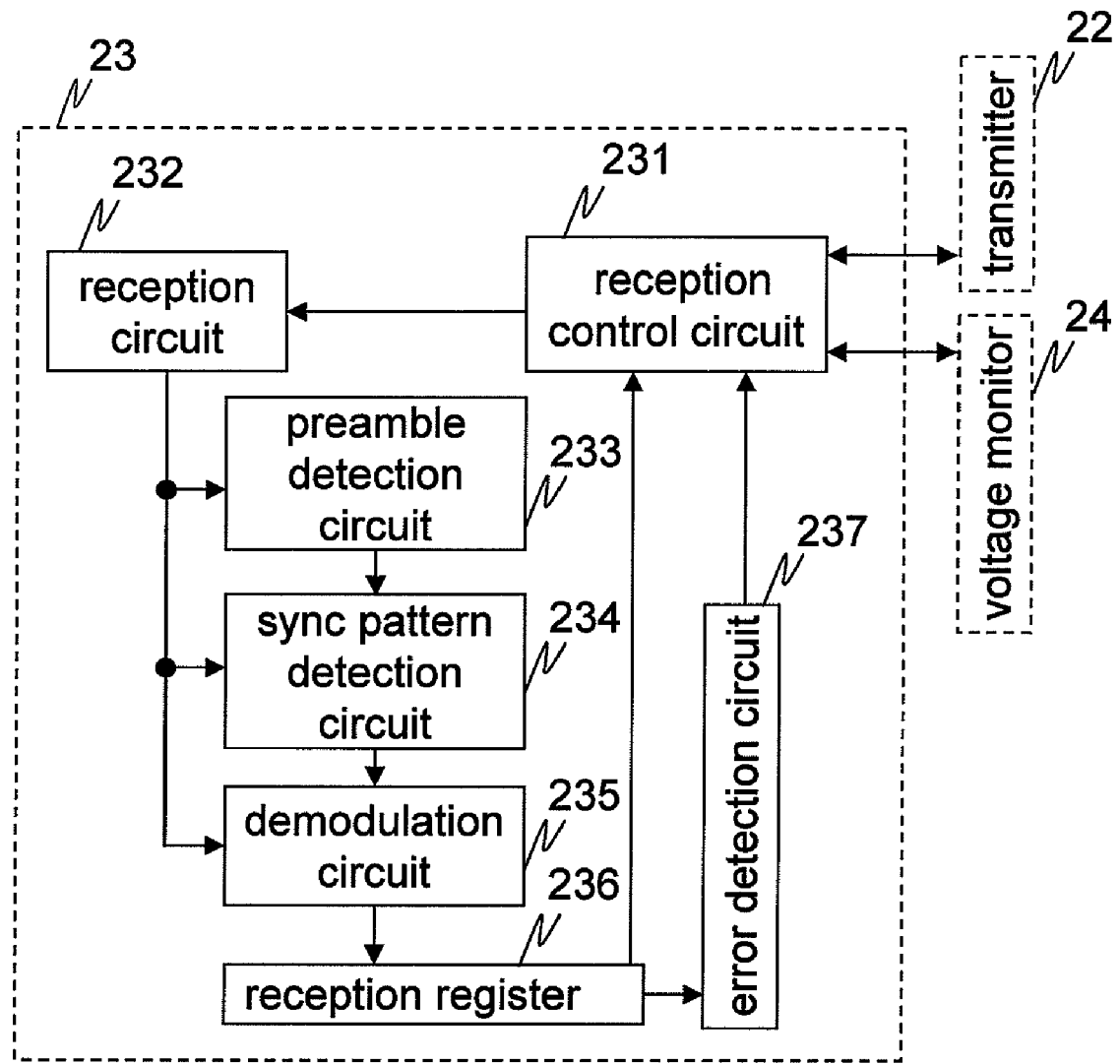
FIG. 5 is a block diagram of a receiver in an embodiment of the present invention.
Figure 6:
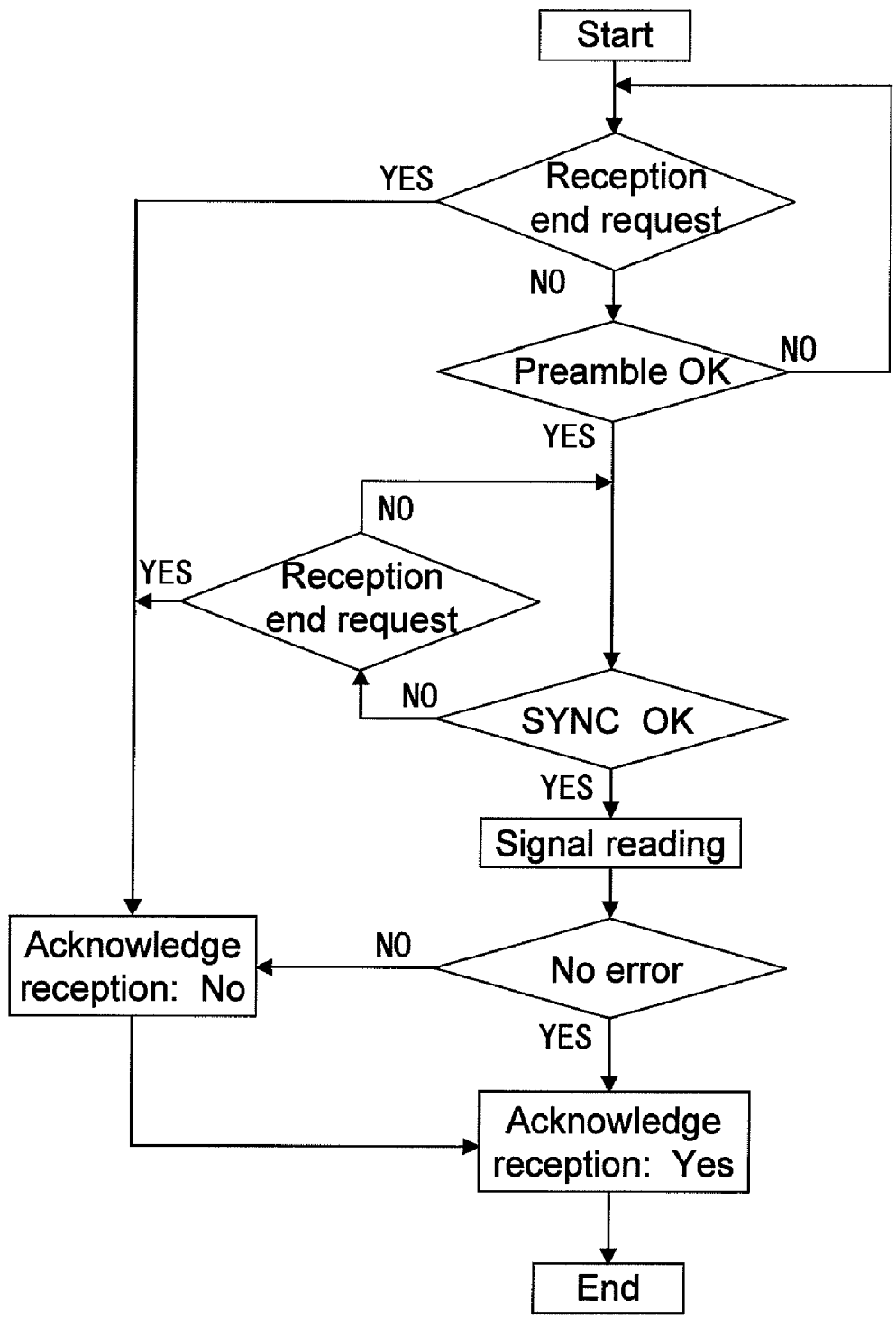
FIG. 6 is a control flowchart of a receiver in an embodiment of the present invention.

As shown in FIG. 5, the receiver 23 has a reception control circuit (reception controller) 231, a reception circuit 232, a preamble detection circuit 233, a sync pattern detection circuit 234, a demodulation circuit 235, a reception register 236, and an error detection circuit 237.

The reception control circuit 231 receives a reception commencement command from the transmitter 22, and controls the reception circuit 232.

The reception circuit 232 performs detection of carrier waves from received signals, gain control, conversion to intermediate frequencies, and other such processing, and transfers the processed data to the preamble detection circuit 233, the sync pattern detection circuit 234, and the demodulation circuit 235.

The preamble detection circuit 233 performs detection of a four-byte continuous preamble pattern. When a preamble pattern is detected, the preamble detection circuit 233 outputs an actuation pulse to the sync pattern detection circuit 234.

The sync pattern detection circuit 234 performs detection of a sync pattern from reception data outputted from the reception circuit 232, by means of the actuation pulse from the preamble detection circuit 233.

The demodulation circuit 235 performs demodulation of reception data using as a reference the sync pattern detected by the sync pattern detection circuit 234.

The reception register 236 stores the reception data demodulated by the demodulation circuit 235. The error detection circuit 237 performs error detection on reception data, and outputs the result to the reception control circuit 231.

Upon receipt of a result notification from the error detection circuit 237, the reception control circuit 231 outputs to the transmitter 22 information to the effect that an acknowledge signal has been received if no error was detected in the reception data and a code indicating an acknowledge signal was present in a specific region of the reception data, or information to the effect that there was no acknowledge signal if a code indicating a non-acknowledge signal was present, and ends the reception operation. The reception control circuit 231 also ends the reception operation when a reception end signal has been received from the transmitter 22.

At this point, information to the effect that there is no acknowledge signal is output to the transmitter 22 if an error was detected in the reception data, or if no preamble pattern, sync pattern, or the like could be detected and the reception data could not be demodulated.

Voltage Monitor 24 Next, the voltage monitor 24 will be described in detail through reference to FIG. 7, which is a block diagram of the voltage monitor 24.

Figure 7:
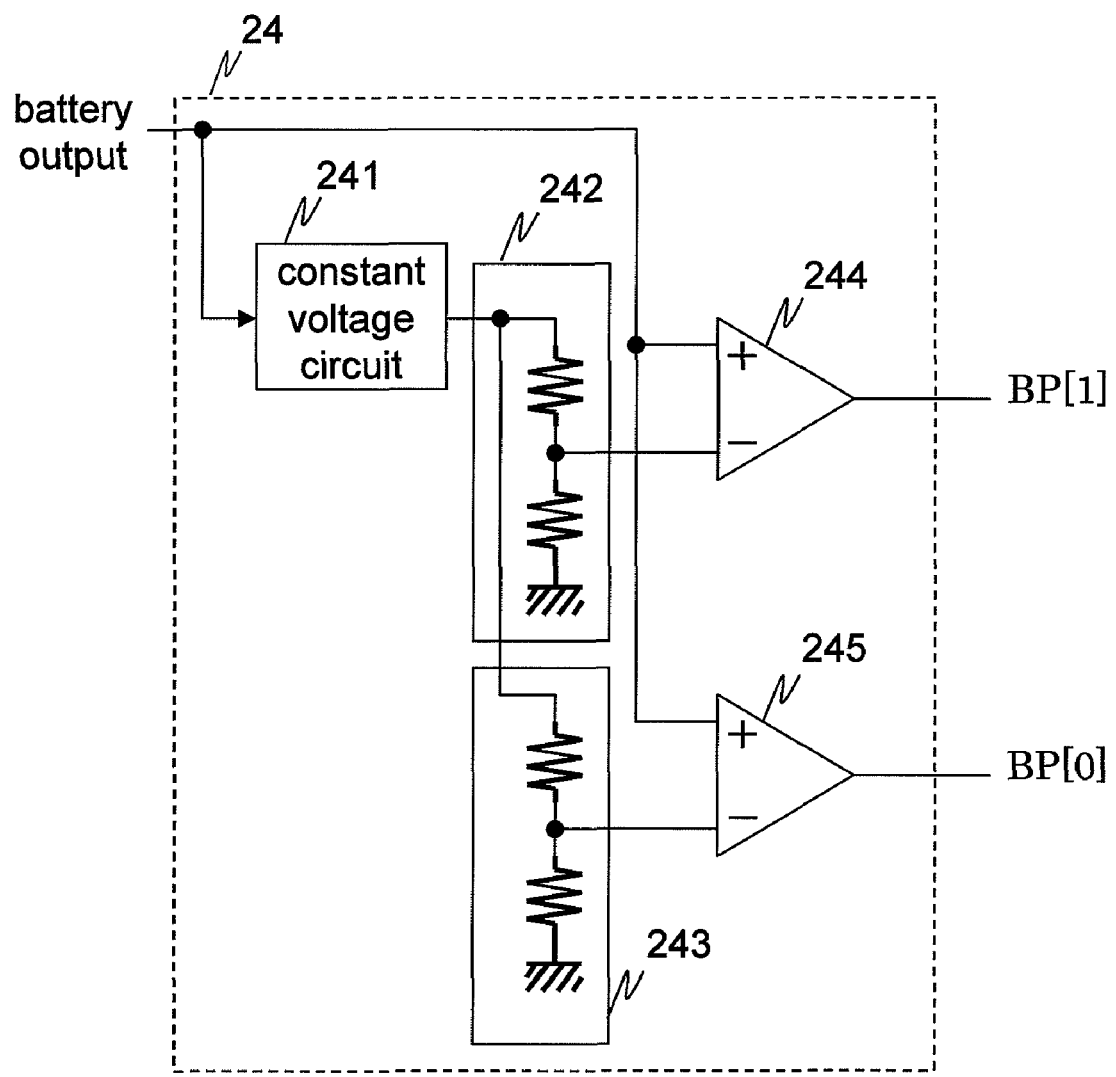
FIG. 7 is a block diagram of a voltage monitor in an embodiment of the present invention.

As shown in FIG. 7, the voltage monitor 24 has a constant voltage circuit 241, a 4_5 V voltage divider circuit 242, a 4_2 V voltage divider circuit 243, a 4_5 comparator 244, and a 4_2 comparator 245.

The output of the battery 26 is inputted to the constant voltage circuit 241, which normally outputs 5 V with respect to an input voltage of 2 to 10 V. A 5 V signal is produced by the constant voltage circuit 241. The 5 V signal produced by the constant voltage circuit 241 is inputted to the 4_5 V voltage divider circuit 242 and the 4_2 V voltage divider circuit 243, and reference voltage signals of 4.5 V and 4.2 V are produced. The 4.5 V reference voltage signal produced by the 4_5 V voltage divider circuit 242 is supplied to the negative terminal of the 4_5 comparator 244 and compared with the output voltage of the battery 26. The 4.2 V reference voltage signal produced by the 4_2 V voltage divider circuit 243 is supplied to the negative terminal of the 4_2 comparator 245 and compared with the output voltage of the battery 26. As a result, the output BP [1:0] of the 4_5 comparator 244 and the 4_2 comparator 245 is "11" hen the output voltage of the battery 26 is greater than 4.5 V, is "01" when the output voltage of the battery 26 is from 4.2 to 4.5 V, and is "00" when this voltage is less than 4.2 V.

Monitoring of the voltage can also be accomplished by digitizing the output of the battery 26 with an A/D converter and reading the digital value with a CPU or the like.

Interface 25

Next, the interface 25 will be described in detail through reference to FIG. 8, which is a block diagram of the interface 25.

Figure 8:
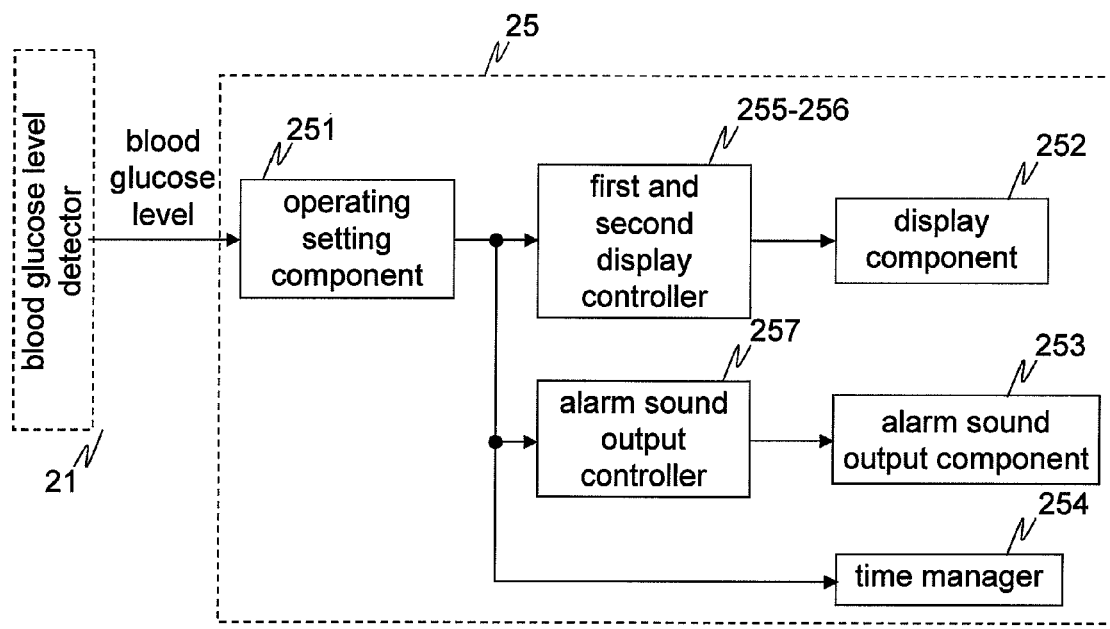
FIG. 8 is a block diagram of an interface in an embodiment of the present invention.

As shown in FIG. 8, the interface 25 has the operating setting component 251, the display component 252, an alarm sound output component 253, a time manager 254, a first display controller 255, a second display controller 256, and an alarm sound output controller 257.

The user adjusts the settings by using the operating setting component 251 while checking the setting categories displayed on the display component 252. The setting categories here include the day of the week, the time, the transmission power, and other such information.

The day of the week and time are outputted to the time manager 254.

The time manager 254 manages the current day of the week and time along with the setting information. The information about day of the week and time managed in the time manager 254 is outputted to the display component 252.

When a blood glucose level is calculated by the blood glucose level detector 21 during the measurement of a blood glucose level, the display component 252 displays the day of the week and time information along with the calculated blood glucose level. If there is a hyperglycemic state in which the calculated blood glucose level is over 400 mg/dL (first reference value), or a hypoglycemic state in which the blood glucose level is under 50 mg/dL (second reference value), the alarm sound output controller 257 objectively determines that the user (diabetes patient) is in an extremely dangerous situation, and controls the alarm sound output component 253 so that an alarm sound is outputted in order to alert the user or any people around the user to this danger. The second display controller 256 takes into account the possibility that the user has lost consciousness, and controls the display component 252 so that an emergency contact telephone number or information related to emergency measures, such as boosting the glucose content in the case of hypoglycemia, is displayed.

Consequently, people around the user of the wireless blood glucose meter 2 can be alerted to the danger to the user. Also, even if the user of the wireless blood glucose meter 2 should lose consciousness, a nearby person can see the telephone number displayed on the display component 252 and immediately call the emergency contact number, or can provide suitable assistance while looking at the treatment method, etc., displayed on the display component 252.

Other Embodiments

An embodiment of the present invention was described above, but the present invention is not limited to or by the above embonvention.

(A)

In the above embodiment, a case of application to the wireless blood glucose meter 2 was described as an example of a biological sample measurement apparatus, but the present invention is not limited to this.

For instance, the measurement apparatus may be one that measures lactic acid, uric acid, or the like, and as long as it is an apparatus that wirelessly transmits this data to another terminal or the like, the effect will be the same as that with the wireless blood glucose meter 2 according to the above embodiment.

(B)

With the wireless blood glucose meter 2 in the above embodiment, an example was given in which when the output voltage of the battery 26 was determined by the voltage monitor 24 to be at least 4.2 V but lower than 4.5 V (second reference voltage) (BP [1:0] of voltage monitor 24=01), the transmission control circuit 221 ended the series of processing without instructing that the blood glucose level outputted from the blood glucose level detector 21 be sent to the portable terminal 3, but the present invention is not limited to this.

For instance, the constitution may be such that the receiver 23 does not receive a response signal from the portable terminal 3 when it has been determined by the voltage monitor 24 that the output voltage of the battery 26 is lower than 4.5 V (second reference voltage) (BP [1:0] of voltage monitor 24=01). At this point, the transmitter 22 does not retransmit the blood glucose level. Consequently, the receiver 23 consumes less power and the service life of the battery 26 can be further extended.

(C)

With the wireless blood glucose meter 2 in the above embodiment, an example was given in which when a blood glucose level was calculated by the blood glucose level detector 21 during measurement of a blood glucose level, the display component 252 displayed the day of the week and time information along with the calculated blood glucose level.

Figure 9A:
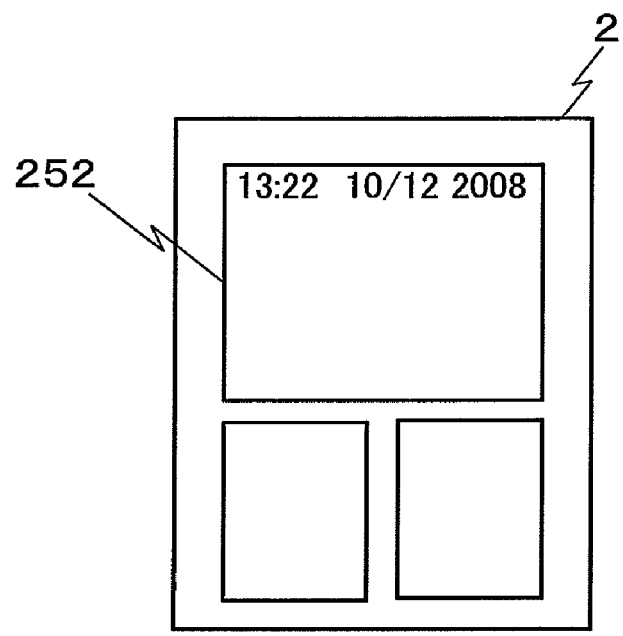
FIGS. 9A and 9B are diagrams illustrating examples of the change in the display state of a wireless blood glucose meter in another embodiment of the present invention.
Figure 9B:
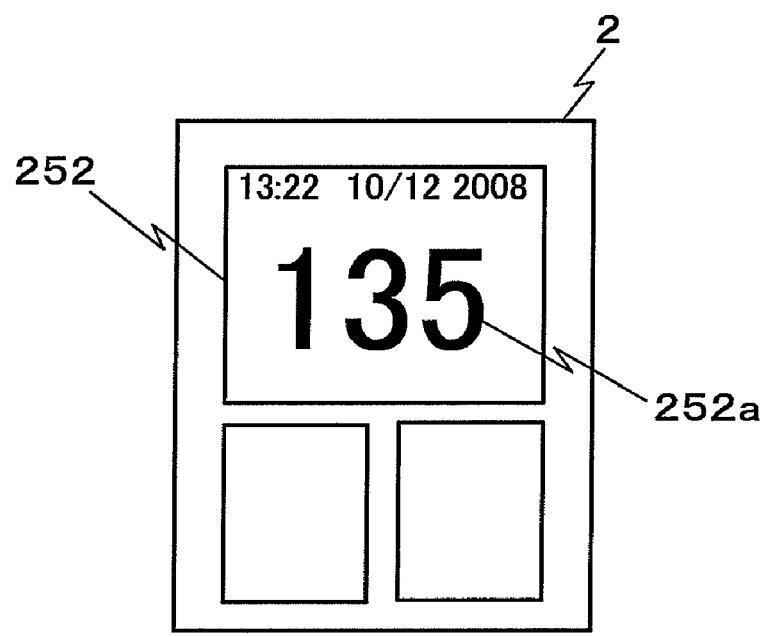
Figure 10:
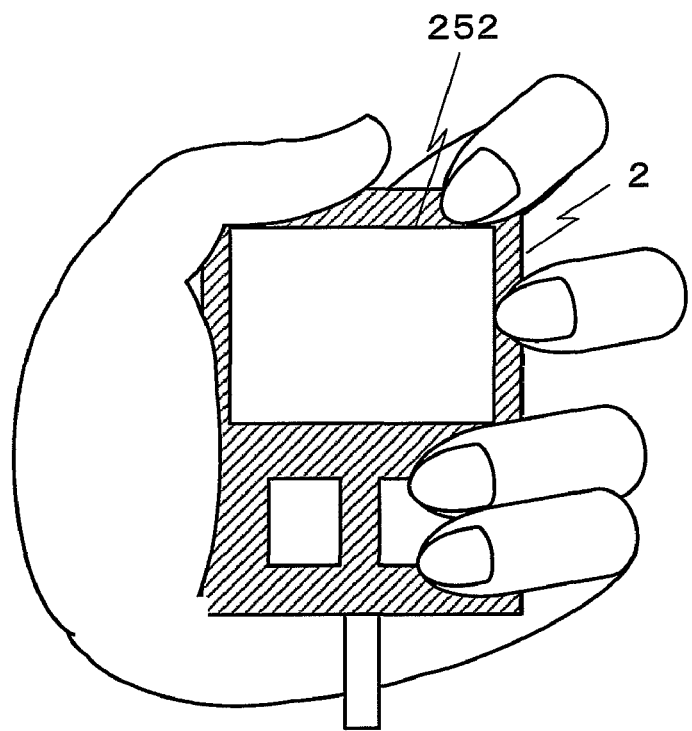
FIG. 10 is a diagram of when the wireless blood glucose meter in FIG. 9 is held in the left hand.
Figure 11:
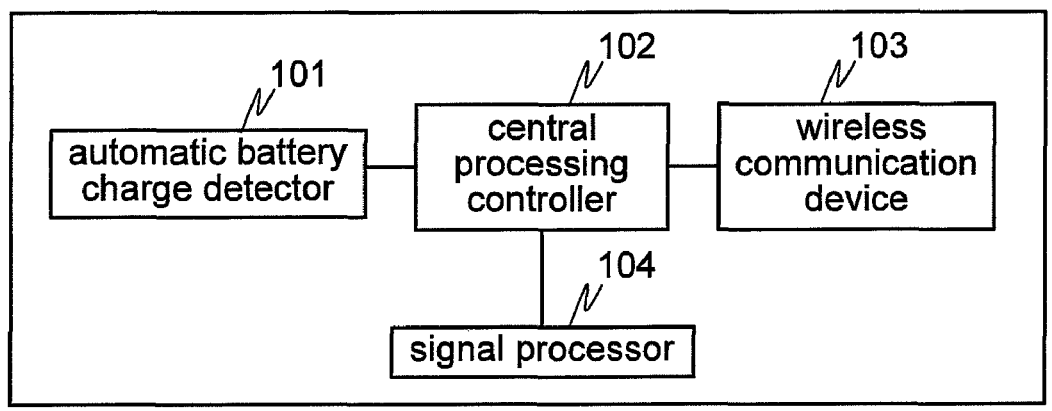
FIG. 11 is a block diagram of a conventional electronic device.

In addition to this, for example, the first display controller 255 (see FIG. 8) may control such that until the transmitter 22 has completed transmission of the blood glucose level, as shown in FIG. 9A, the blood glucose level (biological data) is not displayed (not executed) on the display component 252, and once the transmitter 22 does complete transmission of the blood glucose level, as shown in FIG. 9B, the blood glucose level (biological data) 252a is displayed on the display component 252. Consequently, as shown in FIG. 10, until the transmission of blood glucose level is complete, at least the area around the display component 252 is kept uncovered by the user's hand so that the user can check his or her own blood glucose level. Thus, even with a compact apparatus with which the wireless blood glucose meter 2 is held in the hand during use, since the effect of radio wave absorption by the user's hand can be reduced, the transmission power can be kept low and the service life of the battery 26 can be further extended.

(D)

With the wireless blood glucose meter 2 in the above embodiment, an example was given in which the alarm sound output component 253 and the display component 252 emitted an alarm if the blood glucose level data measured by the blood glucose level detector 21 was at least 400 mg/dL (first reference value) or was under 50 mg/dL (second reference value), but the present invention is not limited to this.

This is merely employing a common indicator for diabetes patients, but the setting may be personalized for the user, such as setting to 350 mg/dL.

Also, regarding the relationship with the first reference value, it is possible to set the conditions according to the indicator of a first reference value serving as a determination reference, such as being the same value or being smaller.

This is merely employing a common indicator for diabetes patients, but the setting may be personalized for the user, such as setting to 60 mg/dL.

Also, regarding the relationship with the second reference value, it is possible to set the conditions according to the indicator of a second reference value serving as a determination reference, such as being the same value or being smaller.

(E)

With the wireless blood glucose meter 2 of the above-mentioned embodiment, an example was given in which the processing was ended without the transmission control circuit 221 instructing that the blood glucose level outputted from the blood glucose level detector 21 be sent to the portable terminal 3, when it was determined by the voltage monitor 24 that the output voltage of the battery 26 was lower than 4.2 V (BP [1:0] of voltage monitor 24=00), but the present invention is not limited to this.

The criterion of 4.2 V for ending processing (the first reference voltage) may instead be 4.0 V or 3.5 V, for example, and the setting value is not important. The first reference voltage can be suitably set as dictated by the performance of the battery or the power consumption of the wireless blood glucose meter.

(F)

With the wireless blood glucose meter 2 of the above-mentioned embodiment, an example was given in which the selector 224 was switched by the transmission control circuit 221 and retransmission was performed when it was determined by the voltage monitor 24 that the output voltage of the battery 26 was at least 4.5 V (BP [1:0] of voltage monitor 24=11), but the present invention is not limited to this.

The criterion of 4.5 V for ending retransmission processing (the second reference voltage) may instead be 5.0 V or 5.5 V, for example, and the setting value is not important. The second reference voltage can be suitably set as dictated by the performance of the battery or the power consumption of the wireless blood glucose meter.

(G)

With the wireless blood glucose meter 2 of the above-mentioned embodiment, an example was given in which the control blocks shown in FIG. 1 were each constructed from a hardware function, but the present invention is not limited to this.

The construction of the control blocks in FIG. 1 may, for example, consist of a single piece of hardware or computer software, or functions of hardware and computer software may be combined. This can be suitably decided according to the processing capability and so forth.

The wireless blood glucose meter according to the present invention is useful as a wireless blood glucose meter with which measurement can be carried out properly even when the battery charge drops low.

The invention claimed is:

1. A battery-powered biological sample measurement apparatus that communicates wirelessly with an external device, comprising:
   a biological data measurement component configured to measure biological data;
   a transmitter configured to transmit the biological data measured by the biological data measurement component to the external device;
   a receiver configured to receive response signals sent from the external device in response to the transmission of the biological data from the transmitter to the external device;
   a voltage monitor configured to monitor the output voltage of the battery; and
   a transmission controller configured to change the transmission method used by the transmitter on the basis of the output voltage of the battery detected by the voltage monitor;
   wherein the transmission controller is configured to control the transmitter so that the transmission of biological data is not executed if the output voltage of the battery as detected by the voltage monitor is lower than a first reference voltage.

2. The biological sample measurement apparatus according to claim 1,
   wherein the transmission controller is configured to control the transmitter so that the retransmission of biological data is executed if the output voltage of the battery as detected by the voltage monitor is equal to or greater than a second reference voltage, when the response signal received by the receiver is not an acknowledge signal indicating that the external device has properly received the biological data, or when the receiver does not receive the response signal within a specific length of time.

3. The biological sample measurement apparatus according to claim 2, wherein the transmission controller is configured to control the transmitter so that biological data is not retransmitted if the output voltage of the battery as detected by the voltage monitor is lower than a second reference voltage and is equal to or greater than the first reference voltage, when the response signal received by the receiver is not the acknowledge signal, or when the receiver does not receive the response signal within the specific length of time.

4. The biological sample measurement apparatus according to claim 3, further comprising a reception controller that is configured to control the receiver so that the response signal is not received if the output voltage of the battery as detected by the voltage monitor is lower than the second reference voltage.

5. The biological sample measurement apparatus according to claim 1, further comprising an interface that has a display component configured to display the biological data measured by the biological data measurement component, an operation setting component that a user is capable of using to make various operation settings, and an alarm sound output component configured to output an alarm sound.

6. The biological sample measurement apparatus according to claim 5, wherein the interface further has a first display controller configured to control the display component so that the biological data is not displayed until the transmitter has completed the transmission of the biological data.

7. The biological sample measurement apparatus according to claim 6, wherein the interface further has an alarm sound output controller configured to control the alarm sound output component so that the alarm sound is outputted when the value of the biological data is equal to or greater than a first reference value, or is less than or equal to a second reference value that is lower than the first reference value.

8. The biological sample measurement apparatus according to claim 7, wherein the interface further has a second display controller configured to control the display component so that an emergency status is displayed when the value of the biological data is equal to or greater than a first reference value, or is less than or equal to a second reference value that is lower than the first reference value.

9. The biological sample measurement apparatus according to claim 8, wherein the second display controller is configured to control the display component to display a telephone number in the emergency status.

10. The biological sample measurement apparatus according to claim 9, wherein the second display controller is configured to control the display component to display a method of treating hyperglycemia or hypoglycemia in the emergency status.

11. The biological sample measurement apparatus according to claim 1, wherein the apparatus is a wireless blood glucose meter configured so that the biological data measurement component measures a blood glucose level.

* * * * *